US006699833B1

(12) United States Patent
Gefter et al.

(10) Patent No.: US 6,699,833 B1
(45) Date of Patent: *Mar. 2, 2004

(54) PHARMACEUTICAL FORMULATIONS FOR SUSTAINED DRUG DELIVERY

(75) Inventors: Malcolm L. Gefter, Lincoln, MA (US); Nicholas Barker, Southborough, MA (US); Gary Musso, Hopkinton, MA (US); Christopher J. Molineaux, Brookline, CA (US)

(73) Assignee: Praecis Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/349,914

(22) Filed: Jul. 8, 1999

Related U.S. Application Data (63) Continuation of application No. 08/762,747, filed on Dec. 11, 1996, now Pat. No. 5,968,895.

(51) Int. Cl.[7] .......................... A61K 38/00; A61K 9/22
(52) U.S. Cl. ........................ 514/2; 514/13; 514/14; 514/15; 514/16; 514/800; 530/313; 530/326; 530/327; 530/328; 530/329; 424/468; 424/488; 424/489; 424/499
(58) Field of Search ........................ 514/2, 13, 14, 514/15, 16, 800; 530/313, 326, 327, 328, 329; 424/468, 486, 488, 489, 499

(56) References Cited

U.S. PATENT DOCUMENTS

| | | | |
|---|---|---|---|
| 4,016,100 A | 4/1977 | Suzuki et al. ................ 252/316 |
| 4,389,393 A | 6/1983 | Schor et al. .................... 424/19 |
| 4,526,938 A | 7/1985 | Churchill et al. ............ 525/415 |
| 4,610,868 A | 9/1986 | Fountain et al. .............. 424/1.1 |
| 4,613,500 A | 9/1986 | Suzuki et al. .................. 429/85 |
| 4,639,370 A | 1/1987 | Carli ............................. 424/80 |
| 4,675,189 A | 6/1987 | Kent et al. .................... 424/490 |
| 4,677,191 A | 6/1987 | Tanaka et al. ............... 528/361 |
| 4,728,721 A | 3/1988 | Yamamoto et al. .......... 528/361 |
| 4,775,535 A | 10/1988 | Lowey ........................ 424/468 |
| 4,789,547 A | 12/1988 | Song et al. .................. 424/449 |
| 4,913,906 A | 4/1990 | Friedman et al. ........... 424/499 |
| 4,980,150 A | 12/1990 | Keith ........................... 424/49 |
| 5,015,479 A | 5/1991 | Mulligan et al. ............ 424/457 |
| 5,028,430 A | 7/1991 | Sanders et al. .............. 424/423 |
| 5,049,395 A | 9/1991 | Chang ......................... 424/494 |
| 5,128,142 A | 7/1992 | Mulligan et al. ............ 424/457 |
| 5,180,522 A | 1/1993 | Kawashima et al. ......... 252/311 |
| 5,192,741 A | 3/1993 | Orsolini et al. ................. 514/4 |
| 5,314,915 A | 5/1994 | Rencher ....................... 514/535 |
| 5,326,571 A | 7/1994 | Wright et al. ................ 424/473 |
| 5,366,734 A | 11/1994 | Hutchinson .................. 424/426 |
| 5,439,688 A | 8/1995 | Orsolini et al. .............. 424/489 |
| 5,462,749 A | 10/1995 | Rencher ...................... 424/484 |
| 5,480,656 A | 1/1996 | Okada et al. ................ 424/493 |
| 5,487,898 A | 1/1996 | Lu et al. ...................... 424/435 |
| 5,520,927 A | 5/1996 | Kim et al. ................... 424/450 |
| 5,540,937 A | 7/1996 | Billot et al. ................. 424/489 |
| 5,545,409 A | 8/1996 | Laurencin et al. .......... 424/426 |
| 5,595,760 A | 1/1997 | Cherif-Cheikh ............. 424/464 |
| 5,629,009 A | 5/1997 | Laurencin et al. .......... 424/426 |
| 5,656,297 A | 8/1997 | Bernstein et al. ........... 424/484 |
| 5,688,530 A | 11/1997 | Bodmer et al. ............. 424/501 |
| 5,700,486 A | 12/1997 | Canal et al. ................ 424/501 |
| 5,711,968 A | 1/1998 | Tracy et al. ................ 424/487 |
| 5,968,895 A | * 10/1999 | Gefter et al. ................... 514/2 |
| 6,180,608 B1 | * 1/2001 | Gefter et al. ................ 514/13 |

FOREIGN PATENT DOCUMENTS

| | | |
|---|---|---|
| DE | 19712718 A1 | 10/1999 |
| EP | 0 328 090 | 8/1989 |
| EP | 0 467 389 | 1/1992 |
| EP | 0 601 799 | 6/1994 |
| EP | 645136 | * 3/1995 |
| FR | 2455459 | 1/1981 |
| JP | 63310827 | 12/1988 |
| WO | WO 88/05661 | 8/1988 |
| WO | WO 92/11844 | 7/1992 |
| WO | WO 92/20349 | 11/1992 |
| WO | WO 94/08566 | 4/1994 |
| WO | WO 94/15587 | 7/1994 |
| WO | WO 96/40757 | 12/1996 |
| WO | WO 97/22357 | 6/1997 |

OTHER PUBLICATIONS

Hussain, M.A. et al., "Injectable Suspensions for Prolonged Release Nalbuphine," *Drug Devel. and Industrial Pharmacy* 17(1):67–76 (1991).

Langer, R. (1982), "Controlled Release of Macromolecules," *Chemtech* 12(2):98–105.

Paavola, A. et al., "Controlled Release of Lidocaine from Injectable Gels and Efficacy in Rat Sciatic Nerve Block," *Pharm. Res.* 12(12):1997–2002 (1995).

(List continued on next page.)

*Primary Examiner*—Christopher S. F. Low
*Assistant Examiner*—Chih-Min Kam
(74) *Attorney, Agent, or Firm*—Lahive & Cockfield, LLP; Guilio A. DeConti, Jr., Esq.; Maria Laccotripe Zacharaki (57) ABSTRACT

Sustained delivery formulations comprising a water-insoluble complex of a peptide and a carrier macromolecule are disclosed. The formulations of the invention allow for loading of high concentrations of peptide in a small volume and for delivery of a pharmaceutically active peptide for prolonged periods, e.g., one month, after administration of the complex. The complexes of the invention can be milled or crushed to a fine powder. In powdered form, the complexes form stable aqueous suspensions and dispersions, suitable for injection. In a preferred embodiment, the peptide of the complex is an LHRH analogue, preferably an LHRH antagonist, and the carrier macromolecule is an anionic polymer, preferably carboxymethylcellulose. Methods of making the complexes of the invention, and methods of using LHRH-analogue-containing complexes to treat conditions treatable with an LHRH analogue, are also disclosed.

36 Claims, 2 Drawing Sheets

OTHER PUBLICATIONS

Palyi, I. et al. (1996), "Effect of Gonadotropin–Releasing Hormone Analogs and Their Conjugates on Gonadotropin–Releasing Hormone Receptor–Positive Human Cancer Cell Lines" *Cancer Detection and Prevention* 20(2):1462–52.

Vincze, B. et al. (1994) "Antitumour Effect of a Gonadotropin–releasing–hormone Antagonist (MI–1544) and its Conjugate on Human Breast Cancer Cells and their Xenografts," *J Cancer Res Clin Oncol.* 120(10):578–84.

* cited by examiner

PHARMACEUTICAL FORMULATIONS FOR SUSTAINED DRUG DELIVERY

This application is a continuation application of Ser. No. 08/762,747 filed on Dec. 11, 1996, now U.S. Pat. No. 5,968,895. The contents of the aforementioned application is hereby incorporated by reference.

BACKGROUND OF THE INVENTION

A variety of diseases and clinical disorders are treated by the administration of a pharmaceutically active peptide. One such example is prostate cancer, which is a sex hormone dependent cancer and which can be treated by administration of a luteinizing hormone releasing hormone (LHRH) analogue that disturbs the production of luteinizing hormone (LH), which regulates the synthesis of male hormones. In particular, to decrease LH production, peptidic analogues of LHRH that act as superagonists of the luteinizing hormone releasing hormone receptor, such as leuprolide and goserelin, have been used.

In many instances, the therapeutic effectiveness of a pharmaceutically active peptide depends upon its continued presence in vivo over prolonged time periods. To achieve continuous delivery of the peptide in vivo, a sustained release or sustained delivery formulation is desirable, to avoid the need for repeated administrations. One approach for sustained drug delivery is by microencapsulation, in which the active ingredient is enclosed within a polymeric membrane to produce microparticles. For example, LHRH superagonists, such as leuprolide and goserelin, typically are encapsulated within a microparticle comprising a polylactide/poly-glycolide copolymer to prepare formulations suitable for depot injection that provide sustained delivery of the superagonist over several weeks to months (see e.g., U.S. Pat. Nos. 4,675,189; 4,677,191; 5,480,656 and 4,728,721).

Additional sustained delivery formulations for administering pharmaceutically active peptides in vivo continuously for prolonged time periods are needed.

SUMMARY OF THE INVENTION

The present invention provides pharmaceutical compositions comprising a stable water-insoluble complex composed of a peptide, preferably a pharmaceutically active peptide, and a carrier macromolecule that allow for sustained delivery of the peptide in vivo upon administration of the complex. Accordingly, the complex of the invention can permit continuous delivery of a pharmaceutically active peptide to a subject for prolonged periods of time, e.g., one month. Moreover, the association of the peptide and the carrier macromolecule in a tight, stable complex allows for loading of high concentrations of the peptide into the formulation.

The complex of the invention is formed by combining the peptide and the carrier macromolecule under conditions such that a water-insoluble complex is formed, e.g., aqueous solutions of the peptide and carrier macromolecule are mixed until the complex precipitates. The complex may be in the form of a solid (e.g., a paste, granules, a powder or a lyophilizate) or the powdered form of the complex can be pulverized finely enough to form stable liquid suspensions or semi-solid dispersions. The complex of the invention is suitable for sterilization, such as by gamma irradiation or electron beam irradiation, prior to administration in vivo.

In a preferred embodiment, the peptide of the water-insoluble complex is an LHRH analogue, more preferably an LHRH antagonist, and the carrier macromolecule is an anionic polymer, preferably carboxymethylcellulose.

Method for treating a subject for a condition treatable with an LHRH analogue by administering to the subject an LHRH-analogue-containing composition of the invention are also provided. In a preferred embodiment, the treatment methods of the invention are used in the treatment of prostate cancer.

DETAILED DESCRIPTION OF THE INVENTION

This invention pertains to pharmaceutical compositions comprising a stable water-insoluble complex composed of a peptide and a carrier macromolecule, methods of making such compositions and methods of using such compositions. The advantages of the pharmaceutical compositions of the invention include the ability for delivery of a pharmaceutically active peptide, either systemically or locally, for prolonged periods (e.g., one month) and the ability to load high concentrations of peptide into the complex.

In order that the invention may be more readily understood, certain terms are first defined.

As used herein, the term "peptide" is intended to include compounds composed of amino acid residues linked by amide bonds. Typically, a peptide will be composed of less than about 100 amino acids, more typically less than about 50 amino acid residues and even more typically, less than about 25 amino acid residues. The term "peptide" is further intended to encompass peptide analogues, peptide derivatives and peptidomimetics that mimic the chemical structure of a peptide composed of naturally-occurring amino acids. Examples of peptide analogues include peptides comprising one or more non-natural amino acids. Examples of peptide derivatives include peptides in which an amino acid side chain, the peptide backbone, or the amino- or carboxy-terminus has been derivatized (e.g., peptidic compounds with methylated amide linkages). Examples of peptidomimetics include peptidic compounds in which the peptide backbone is substituted with one or more benzodiazepine molecules (see e.g., James, G. L. et al. (1993) *Science* 260:1937–1942), "inverso" peptides in which all L-amino acids are substituted with the corresponding D-amino acids, "retro-inverso" peptides (see U.S. Pat. No. 4,522,752 by Sisto) in which the sequence of amino acids is reversed ("retro") and all L-amino acids are replaced with D-amino acids )"inverso") and other isosteres, such as peptide backbone (i.e., amide bond) mimetics, including modifications of the amide nitrogen, the α-carbon, amide carbonyl, complete replacement of the amide bond, extensions, deletions or backbone crosslinks. Several peptide backbone modifications are known, including $\psi[CH_2S]$, $\psi[CH_2NH]$, $\psi[CSNH_2]$, $\psi[NHCO]$, $\psi[COCH_2]$, and $\psi[(E)$ or $(Z)$ $CH=CH]$. In the nomenclature used above, $\psi$ indicates the absence of an amide bond. The structure that replaces the amide group is specified within the brackets. Other possible modifications include an N-alkyl (or aryl) substitution (ψ[CONR]), backbone crosslinking to construct lactams and other cyclic structures, and other derivatives including C-terminal hydroxymethyl derivatives, O-modified derivatives and N-terminally modified derivatives including substituted amides such as alkylamides and hydrazides.

As used herein, the term "pharmaceutically active peptide" is intended to refer to a peptide that exhibits pharmacologic activity, either in its present form or upon processing in vivo (i.e., pharmaceutically active peptides include peptides with constitutive pharmacologic activity and peptides in a "prodrug" form that have to be metabolized or processed in some way in vivo following administration in order to exhibit pharmacologic activity).

As used herein, the terms "multivalent cationic peptide" and "multivalent anionic peptide" are intended to refer to peptides comprising a multiplicity of positive or negative charges, respectively. A "bivalent cationic" or "bivalent anionic" peptide is intended to refer to a peptide comprising two positive or negative charges, respectively. A "trivalent cationic" or "trivalent anionic" peptide is intended to refer to a peptide comprising three positive or negative charges, respectively.

As used herein, the term "LHRH analogue" is intended to encompass peptidic compounds that mimic the structure of luteinizing hormone releasing hormone. An LHRH analogue may be an LHRH agonist or an LHRH antagonist.

As used herein, an "LHRH agonist" is intended to refer to a compound which stimulates the luteinizing hormone releasing hormone receptor (LHRH-R) such that release of luteinizing hormone is stimulated, or an "LHRH antagonist", which refers to a compound that inhibits LHRH-R such that release of luteinizing hormone is inhibited. Examples of LHRH agonists include leuprolide (trade name: Lupron®; Abbott/TAP), goserelin (trade name: Zoladex®; Zeneca), buserelin (Hoechst), triptorelin (also known as Decapeptyl, D-Trp-6-LHRH and Debiopharm®; Ipsen/Beaufour), nafarelin (trade name" Synarel®; Syntex), lutrelin (Wyeth), cystorelin (Hoechst), gonadorelin (Ayerst) and histrelin (Ortho).

As used herein, the term "LHRH antagonist" is intended to refer to a compound that inhibits the luteinizing hormone releasing hormone receptor such that release of luteinizing hormone is inhibited. Examples of LHRH antagonists include Antide, Cetrorelix, compounds described in U.S. Pat. No. 5,470,947 to Folkers et al.; PCT Publication No. WO 89/01944 by Folkers et al.; U.S. Pat. No. 5,413,990 to Haviv; U.S. Pat. No. 5,300,492 to Haviv; U.S. Pat. No. 5,371,070 to Koerber et al.; U.S. Pat. No. 5,296,468 to Hoeger et al.; U.S. Pat. No. 5,171,835 to Janaky et al.; U.S. Pat. No. 5,003,011 to Coy et al.; U.S. Pat. No. 4,431,635 to Coy; U.S. Pat. No. 4,992,421 to De et al.; U.S. Pat. No. 4,851,385 to Roeske; U.S. Pat. No. 4,801,577 to Nestor, Jr. et al.; and U.S. Pat. No. 4,689,396 to Roeske et al. and compounds disclosed in U.S. patent application Ser. No. 08/480,494, entitled "LHRH Antagonist Peptides", and a corresponding PCT application thereof (PCT Application No. PCT/US96/09852), also entitled "LHRH Antagonist Peptides", the entire contents of both of which are expressly incorporated herein by reference. An especially preferred LHRH antagonist comprises the structure: Ac-D-Nal$^1$, 4-Cl-D-Phe$^2$, D-Pal$^3$, N-Me-Tyr$^5$, D-Asn$^6$, Lys(iPr)$^8$, D-Ala$^{10}$-LHRH, referred to herein as PPI-149.

As used herein, the term "carrier macromolecule" is intended to refer to a macromolecule that can complex with a peptide to form a water-insoluble complex. Preferably, the macromolecule has a molecular weight of at least 5 kDa, more preferably 10 kDa. The term "anionic carrier macromolecule" is intended to include negatively charged high molecular weight molecules, such as anionic polymers. The term "cationic carrier macromolecule" is intended to includes positively charged high molecular weight molecules, such as cationic polymers.

As used herein, the term "water-insoluble complex" is intended to refer to a physically and chemically stable complex that forms upon appropriate combining of a peptide and carrier macromolecule according to procedures described herein. This complex typically takes the form of a precipitate that is produced upon combining aqueous preparations of the peptide and carrier macromolecule. Although not intending to be limited by mechanism, the formation of preferred water-insoluble complexes of the invention is thought to involve (i.e., be mediated at least in part by) ionic interactions in situations where the peptide is cationic and the carrier molecule is anionic or vice versa. Additionally or alternatively, the formation of a water-insoluble complex of the invention may involve (i.e., be mediated at least in part by) hydrophobic interactions. Still further, formation of a water-insoluble complex of the invention may involve (i.e., be mediated at least in part by) covalent interactions. Description of the complex as being "water-insoluble" is intended to indicate that the complex does not substantially or readily dissolve in water, as indicated by its precipitation from aqueous solution. However, it should be understood that a "water-insoluble" complex of the invention may exhibit limited solubility in water either in vitro or in the aqueous physiological environment in vivo.

As used herein, the term "sustained delivery" is intended to refer to continual delivery of a pharmaceutical agent in vivo over a period of time following administration, preferably at least several days, a week or several weeks. Sustained delivery of the agent can be demonstrated by, for example, the continued therapeutic effect of the agent over time (e.g., for an LHRH analogue, sustained delivery of the analogue can be demonstrated by continued suppression of testosterone synthesis over time). Alternatively, sustained delivery of the agent may be demonstrated by detecting the presence of the agent in vivo over time.

As used herein, the term "subject" is intended to include is intended to include warm-blooded animals, preferably mammals, most preferably humans.

As used herein, the term "administering to a subject" is intended to refer to dispensing, delivering or applying a composition (e.g., pharmaceutical formulation) to a subject by any suitable route for delivery of the composition to the desired location in the subject, including delivery by either the parenteral or oral route, intramuscular injection, subcutaneous/intradermal injection, intravenous injection, buccal administration, transdermal delivery and administration by the rectal, colonic, vaginal, intranasal or respiratory tract route.

As used herein, the term "a condition treatable with an LHRH analogue" is intended to include diseases, disorders and other conditions in which administration of an LHRH agonist or LHRH antagonist has a desired effect, e.g., a therapeutically beneficial effect. Examples of conditions treatable with an LHRH analogue include hormone-dependent cancers (including prostate cancer, breast cancer, ovarian cancer, uterine cancer and testicular cancer), benign prostatic hypertrophy, precocious puberty, endometriosis, uterine fibroids, infertility (through in vitro fertilization) and fertility (i.e., contraceptive uses).

One aspect of the present invention pertains to a pharmaceutical composition comprising a water-insoluble complex of a pharmaceutically active peptide and a carrier macromolecule. In a preferred embodiment, formation of the water-insoluble complex is mediated at least in part by ionic interactions between the pharmaceutically active peptide and the carrier macromolecule. In these embodiments, either the pharmaceutically active peptide is cationic and the carrier macromolecule is anionic or the pharmaceutically active peptide is anionic and the carrier macromolecule is cationic. In another embodiment, formation of the water-insoluble complex is mediated at least in part by hydrophobic interactions between the pharmaceutically active peptide and the carrier macromolecule. In a preferred embodiment, the peptide used in the complex is a multivalent cationic peptide, such as a bivalent or trivalent cationic peptide and the carrier macromolecule is an anionic macromolecule.

The pharmaceutical compositions of the invention permit sustained delivery of the peptide to a subject in vivo after administering the composition to the subject, wherein the duration of the sustained delivery can be varied depending upon the concentration of peptide and carrier macromolecule used to form the complex. For example, in one embodiment, the water-insoluble complex provides sustained delivery of the peptide to a subject for at least one week after the pharmaceutical composition is administered to the subject. In another embodiment, the water-insoluble complex provides sustained delivery of the peptide to a subject for at least two weeks after the pharmaceutical composition is administered to the subject. In yet another one embodiment, the water-insoluble complex provides sustained delivery of the peptide to a subject for at least three weeks after the pharmaceutical composition is administered to the subject. In still another embodiment, the water-insoluble complex provides sustained delivery of the peptide to a subject for at least four weeks after the pharmaceutical composition is administered to the subject. Formulations that provide sustained delivery for longer or shorter durations are also encompassed by the invention, such as formulations that provide continuous delivery for 1 day, 1–7 days, one month, two months, three months, and the like.

Any size peptide may be suitable for use in the complex as long as the peptide has the ability to form a water-insoluble noncovalent complex with the carrier macromolecule upon combination of the peptide and carrier macromolecule. However, in certain preferred embodiments, the peptide is about 5 to about 20 amino acids in length, about 8 to about 15 amino acids in length or about 8 to about 12 amino acids in length. A variety of pharmaceutically active peptides may be used in the formulations, non-limiting examples of which include LHRH analogues (discussed further below), bradykinin analogues, parathyroid hormone, adenocorticotrophic hormone (ACTH), calcitonin, and vasopressin analogues (e.g., 1-deamino-8-D-arginine vasopressin (DDAVP)).

Although a variety of carrier macromolecules may be suitable for formation of the water-insoluble complexes of the invention, preferred macromolecules are polymers. In a preferred embodiment, the carrier macromolecule is an anionic polymer, such as an anionic polyacohol derivative, or fragment thereof. Anionic moieties with which the polyalcohol can be derivatized include, for example, carboxylate, phosphate or sulfate groups. A particularly preferred anionic polymer is an anionic polysaccharide derivative, or fragment thereof. The carrier macromolecule may comprise a single molecular species (e.g., a single type of polymer) or two or more different molecular species (e.g., a mixture of two types of polymers). Examples of specific anionic polymers include carboxymethylcellulose, algin, alginate, anionic acetate polymers, anionic acrylic polymers, xantham gums, sodium starch glycolate, and fragments, derivatives and pharmaceutically acceptable salts thereof, as well as anionic carageenan derivatives, anionic polygalacturonic acid derivatives, and sulfated and sulfonated polystyrene derivatives. Examples of cationic polymers include poly-L-lysine and other polymers of basic amino acids.

In a particularly preferred embodiment of the invention, the peptide of the water-insoluble complex is an LHRH analogue, for example an LHRH agonist or, more preferably, an LHRH antagonist. Such LHRH analogues typically are 10 amino acids in length. Preferred LHRH antagonists include LHRH antagonists that comprise a peptide compound, wherein a residue of the peptide compound corresponding to the amino acid at position 6 of natural mammalian LHRH comprises a D-asparagine (D-Asn) structure. As used herein, the term "D-asparagine structure" is intended to include D-Asn and analogues, derivatives and mimetic thereof that retain the functional activity of D-Asn. Other preferred LHRH antagonists include LHRH antagonists that comprise a peptide compound comprising a structure:

A-B-C-D-E-F-G-H-I-J wherein

A is pyro-Glu, Ac-D-Nal , Ac-D-Qal, Ac-Sar, or Ac-D-Pal

B is His or 4-Cl-D-Phe

C is Trp, D-Pal, D-Nal, L-Nal, D-Pal(N-O), or D-Trp

D is Ser

E is N-Me-Ala, Tyr, N-Me-Tyr, Ser, Lys(iPr), 4-Cl-Phe, His, Asn, Met, Ala, Arg or Ile;

F is wherein

R and X are, independently, H or alkyl; and

L comprises a small polar moiety, with the proviso that F is not D-Cit, D-Hci or a lower alkyl derivative of D-Cit or D-Hci;

G is Leu or Trp;

H is Lys(iPr), Gln, Met, or Arg

I is Pro; and

J is Gly-NH$_2$ or D-Ala-NH$_2$;

or a pharmaceutically acceptable salt thereof.

Preferably, F is selected from the group consisting of D-Asn, D-Gln and D-Thr. More preferably, F is D-Asn. Preferably, E is tyrosine (Tyr) or N-methyl-tyrosine (N-Me-Tyr). In a particularly preferred embodiment, the LHRH antagonist has the following structure: Ac-D-Nal$^1$, 4-Cl-D-Phe$^2$, D-Pal$^3$, N-Me-Tyr$^5$, D-Asn$^6$, Lys(iPr)$^8$, D-Ala$^{10}$-LHRH (referred to herein as PPI-149). A particularly preferred complex of the invention comprises PPI-149 and carboxymethylcellulose.

In addition to the water-insoluble complex, the pharmaceutical formulations of the invention can comprise additional pharmaceutically acceptable carriers and/or excipients. As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous or parenteral administration (e.g., by injection). Excipients include pharmaceutically acceptable stabilizers and disintegrants.

In addition to pharmaceutical formulations of LHRH analogues complexed with a carrier macromolecule, the invention further encompasses packaged formulations containing such complexes and syringes containing such complexes. For example, the invention provides a packaged formulation for treating a subject for a condition treatable with an LHRH analogue, comprising a water-insoluble complex of an LHRH analogue (preferably PPI-149) and a carrier macromolecule (preferably carboxymethylcellulose), packaged with instructions for using the water-insoluble complex for treating a subject for a condition treatable with an LHRH analogue. In another embodiment, the invention provides a syringe having a lumen, wherein a water-insoluble complex of an LHRH analogue (preferably PPI-149) and a carrier macromolecule (preferably, carboxymethyl-cellulose) is included in the lumen.

The complex of the invention is prepared by combining the peptide and the carrier macromolecule under conditions such that a water-insoluble complex of the peptide and the carrier macromolecule forms. Accordingly, another aspect of the invention pertains to methods for preparing pharmaceutical formulations. In one embodiment, the method comprises:

providing a peptide and a carrier macromolecule;

combining the peptide and the carrier macromolecule under conditions such that a water-insoluble complex of the peptide and the carrier macromolecule forms; and preparing a pharmaceutical formulation comprising the water-insoluble complex. For example, a solution of the peptide and a solution of the carrier macromolecule are combined until a water-insoluble complex of the peptide and the carrier macromolecule precipitates out of solution. In certain embodiments, the solutions of the peptide and the carrier macromolecule are aqueous solutions. Alternatively, if the peptide or the carrier molecule (or both) is not substantially water soluble prior to combination the two, then the peptide and/or carrier macromolecule can be dissolved in a water-miscible solvent, such as an alcohol (e.g., ethanol) prior to combining the two components of the complex. In another embodiment of the method of preparing the water-insoluble complex, the solution of the peptide and the solution of the carrier macromolecule are combined and heated until a water-insoluble complex of the peptide and the carrier macromolecule precipitates out of solution. The amounts of peptide and carrier macromolecule necessary to achieve the water-insoluble complex may vary depending upon the particular peptide and carrier macromolecule used, the particular solvent(s) used and/or the procedure used to achieve the complex. Typically, however, the peptide will be in excess relative to the anionic molecule on a molar basis. Often, the peptide also will be in excess on a weight/weight basis, as demonstrated in the Examples. In certain embodiments, the carrier macromolecule, preferably carboxymethylcellulose, and the peptide, preferably PPI-149, are combined at a ratio of 0.2:1 (w/w) of carrier macromolecule:peptide. In various other embodiments, the ratio of carrier macromolecule to peptide (w/w) can be, for example, 0.5:1, 0.4:1, 0.3:1, 0.25:1, 0.15:1 or 0.1:1. Non-limiting examples of conditions and procedures for preparing a water-insoluble complex of the invention are described further in Example 1–5.

Once the peptide/macromolecule complex precipitates out of solution, the precipitate can be removed from the solution by means known in the art, such as filtration (e.g., through a 0.45 micron nylon membrane), centrifugation and the like. The recovered paste then can be dried (e.g., in vacuo or in a 70° C. oven) and the solid can be milled or pulverized to a powder by means known in the art (e.g., hammer or gore milling, or grinding in mortar and pestle). Alternatively, the paste can be frozen and lyophilized to dryness. The powder form of the complex can be dispersed in a carrier solution to form a liquid suspension or semi-solid dispersion suitable for injection. Accordingly, in various embodiments, a pharmaceutical formulation of the invention is a lyophilized solid, a liquid suspension or a semi-solid dispersion.

In another embodiment, the pharmaceutical formulation of the invention is sterile formulation. For example, following formation of the water-insoluble complex, the complex can be sterilized, optimally by gamma irradiation or electron beam sterilization. Accordingly, the method of the invention for preparing a pharmaceutical formulation described above can further comprise sterilizing the water-insoluble complex by gamma irradiation or electron beam irradiation. Alternatively, to prepare a sterile pharmaceutical formulation, the water-insoluble complex can be isolated using conventional sterile techniques (e.g., using sterile starting materials and carrying out the production process aseptically). Accordingly, in another embodiment of the method for preparing a pharmaceutical formulation described above, the water-insoluble complex is formed using aseptic procedures.

Methods of forming a water-insoluble complex of the invention are described further in Examples 1–5. Pharmaceutical formulations, including powders, liquid suspensions, semi-solid dispersions, lyophilized solids, and sterilized forms thereof (e.g., by gamma irradiation), prepared according to the methods of the invention, are also encompassed by the invention.

Yet another aspect of the invention pertains to methods of using the pharmaceutical formulations of the invention to treat a subject suffering from a condition treatable by the pharmaceutically active peptide included in the water-insoluble complex. Accordingly, in a preferred embodiment, the invention provides a method for treating a subject for a condition treatable with an LHRH analogue, comprising administering to the subject a pharmaceutical formulation comprising a water-insoluble complex of an LHRH analogue and a carrier macromolecule.

The pharmaceutical formulation can be administered to the subject by any route suitable for achieving the desired therapeutic result(s), although preferred routes of administration are parenteral routes, in particular intramuscular (i.m.) injection and subcutaneous/intradermal (s.c./i.d.) injection. Alternatively, the formulation can be administered to the subject orally. Other suitable parental routes include intravenous injection, buccal administration, transdermal delivery and administration by the rectal, vaginal, intranasal or respiratory tract route. It should be noted that when a formulation that provides sustained delivery for weeks to months by the i.m or s.c./i.d. route is administered by an alternative route, there may not be sustained delivery of the agent for an equivalent length of time due to clearance of the agent by other physiological mechanisms (i.e., the dosage form may be cleared from the site of delivery such that prolonged therapeutic effects are not observed for time periods as long as those observed with i.m or s.c./i.d. injection).

The pharmaceutical formulation contains a therapeutically effective amount of the LHRH analogue. A "therapeutically effective amount" refers to an amount effective, at dosages and for periods of time necessary, to achieve the desired result. A therapeutically effective amount of an LHRH analogue may vary according to factors such as the disease state, age, and weight of the individual, and the ability of the LHRH analogue (alone or in combination with one or more other drugs) to elicit a desired response in the individual. Dosage regimens may be adjusted to provide the optimum therapeutic response. A therapeutically effective amount is also one in which any toxic or detrimental effects of the antagonist are outweighed by the therapeutically beneficial effects. A non-limiting range for a therapeutically effective amount of an LHRH analogue is 0.01 to 10 mg/kg. It is to be noted that dosage values may vary with the severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The treatment method of the invention can be applied to the treatment of various conditions, diseases and disorders in which administration of an LHRH analogue has a desired clinical effect. Examples of disease and disorders include hormone-dependent cancers, such as prostate cancer, breast cancer, ovarian cancer, uterine cancer and testicular cancer, benign prostatic hypertrophy, precocious puberty, endometriosis and uterine fibroids. Accordingly, the invention provides methods of treating these diseases and disorders by administering a pharmaceutical formulation of the invention. Additionally, LHRH analogues can be used to alter fertility. Accordingly, the methods of the invention also can be used in vitro fertilization and contraceptive purposes.

In a particularly preferred embodiment, the method is used to treat prostate cancer, the LHRH analogue used in the formulation is an LHRH antagonist, most preferably PPI-149, and the method allows for sustained delivery of the LHRH analogue in vivo for at least four weeks after administration by intramuscular or subcutaneous administration. An LHRH analogue, preferably PPI-149, formulated according to the invention can be used to inhibit growth of prostate cancer cells by administering the LHRH analogue to a subject suffering from prostate cancer. Moreover, an LHRH antagonist, preferably PPI-149, formulated according to the invention, can be used to inhibit the testosterone surge that accompanies the use of an LHRH agonist by preadministering the LHRH antagonist, preferably PPI-149, to a subject suffering from prostate cancer before initiating LHRH agonist therapy. Methods for inhibiting LHRH agonist-induced testosterone surge, and other methods for treating prostate cancer using LHRH antagonist, to which the formulations of the present invention can be applied, are described further in U.S. patent application Ser. No. 08/573,109, entitled "Methods for Treating Prostate Using LHRH Antagonists", filed Dec. 15, 1995, and a continuation-in-part patent application thereof, Ser. No. 08/755,593, also entitled "Methods for Treating Prostate Cancer Using LHRH Antagonists", filed Nov. 25, 1996, the entire contents of both of which are expressly incorporated herein by reference.

Specific processes for complexing a pharmaceutically active peptide with an carrier macromolecules are set forth in Examples 1–5 below. Also described are test results that demonstrate that an LHRH antagonist-containing complex can enable sustained delivery of the pharmaceutically active peptide in vivo (Example 6) and can inhibit LHRH-agonist induced testosterone surge (Example 7). The following examples, which further illustrate the invention, should not be construed as limiting. The contents of all references, patents and published patent applications cited throughout this application are hereby incorporated by reference.

EXAMPLE 1

A 100 ml solution of the LHRH antagonist PPI-149 was prepared by dissolving 6.25 mg/ml of PPI-149 in water. An equal sample (100 ml minimum) of USP carboxymethylcellulose sodium (CMC) (low viscosity grade, Hercules Chemical Co.) was prepared at 0.125% w/v and mixed until dissolved. Equal portions of the PPI-149 and CMC solutions were mixed (giving a CMC:peptide ratio of 0.2:1 (w/w)) and a solid material was obtained. The solid material was stirred overnight and then collected by filtration over a 0.45 micron nylon filter. HPLC evaluation of the solution filtrate indicated at least 95% of the PPI-149 compound was converted to the solid complex, was removed from solution. The recovered white paste was rinsed twice with water and then transferred to a vial and dried in vacuo. Upon drying for 72 hours, 633 mg of a white powder was obtained. The solid material was then powdered in a mortar and pestle. Elemental analysis indicated 57% peptide in the complex.

EXAMPLE 2

25 mg of PPI-149 was dissolved in 1 ml of water. To this was added 1 ml of a 0.5% carboxymethylcellulose solution. The mixture formed a silky white solid upon mixing. The mixture was heated to reflux for five minutes and a flocculent white precipitate was formed. This material was isolated by centrifugation/decantation. The solid was resuspended in water and collected by repeated centrifugation. HPLC evaluation of the solution filtrate indicated at least 90% of the PPI-149 compound was converted to the solid complex. The white precipitate was dried in vacuo and the solid material was comminuted in a mortar and pestle. Elemental analysis indicated 77% peptide in the complex.

EXAMPLE 3

50mg of PPI-149 was dissolved in 2 mL of 5% mannitol and mixed with 2 mL of 0.5% carboxymethylcellulose (low viscosity, USP, Spectrum Quality Chemicals). The mixture was stirred and immediately yielded a white precipitate. The suspension was frozen and lyophilized to dryness to yield a PPI-149 sustained delivery complex.

EXAMPLE 4

25 mg of PPI-149 was dissolved in 1 mL water. To this was added 1 mL of 0.5% sodium alginate, USP (Spectrum). The mixture immediately formed a white precipitate upon mixing. This material was isolated by centrifugation/decantation. The solid was resuspended in water and collected by repeated centrifugation. The white precipitate was dried in vacuo. Elemental analysis was performed to obtain a peptide content of 66%.

EXAMPLE 5

25 mg of PPI-149 was dissolved in 1 mL water. Ammonia was added to adjust the pH to 11.0. To this was added 1 mL of 0.5% alginic acid, USP (Spectrum). The mixture immediately formed a white precipitate upon mixing. This material was isolated by centrifugation/decantation. The solid was resuspended in water and collected by repeated centrifugation. The white precipitate was dried in vacuo. Elemental analysis was performed to obtain a peptide content of 79%.

EXAMPLE 6

Figure 1A:
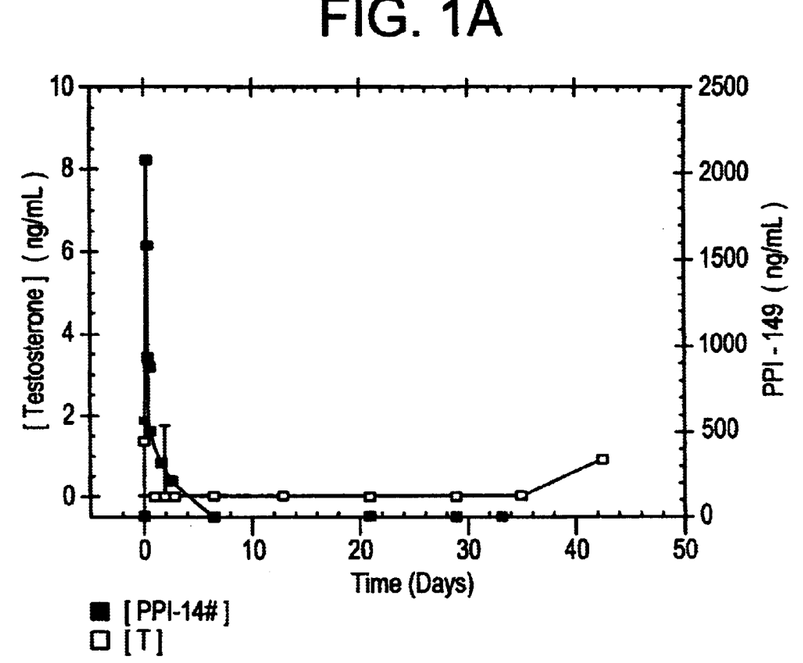
FIG. 1 shows graphs depicting the plasma testosterone levels (in ng/ml; open black boxes) and plasma PPI-149 levels (in ng/ml; closed boxes) in rats (left graph) and dogs (right graph) over time following intramuscular injection of a complex of PPI-149 and carboxymethylcellulose.
Figure 1B:
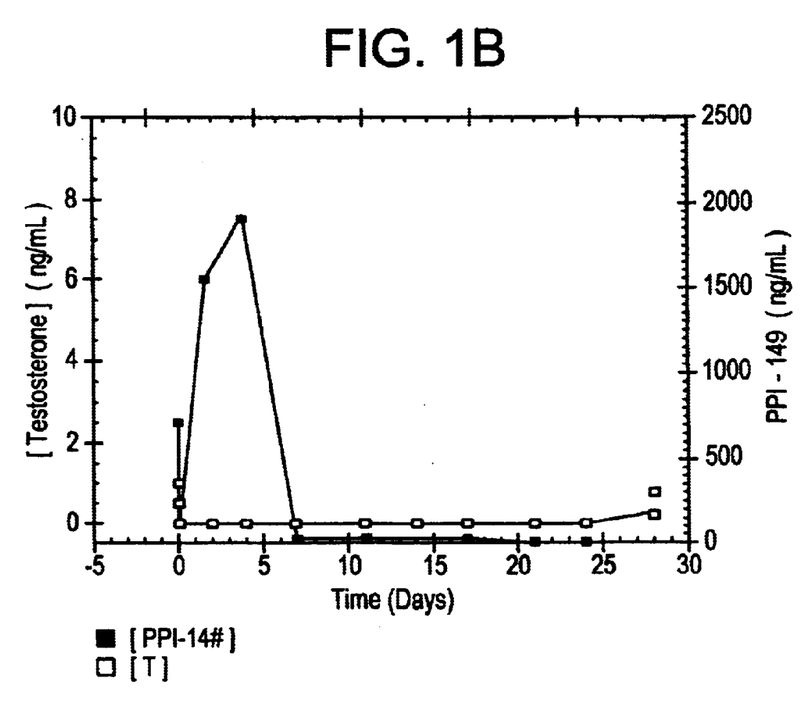

A water-insoluble complex of the LHRH antagonist PPI-149 and carboxymethylcellulose was prepared according to the preceding examples. A suspension of the PPI-149/CMC complex was prepared and a single dose was injected intramuscularly into rats and dogs. The dosage for the rats was 50 $\mu$g/kg/day×60 days and the dosage for the dogs was 40 $\mu$g/kg/day×28 days. Plasma testosterone levels (in ng/ml) were determined at various time points as a measure of the activity of the LHRE antagonist in the animal. Representative results, shown in the graph of FIG. 1, demonstrate that intramuscular injection of the PPI-149/CMC complex leads to sustained suppression of plasma testosterone levels for at least 42 days in the rats and at least 28 days in the dogs (indicated by the open boxes in FIG. 1), demonstrating sustained delivery of the LHRH antagonist. Plasma levels of PPI-149 (in ng/ml) were also monitored in the animals (indicated by the closed boxes in FIG. 1). An initial spike of PPI-149 was observed for about the first eight days, after which time PPI-149 was essentially undetectable in the plasma. Despite the inability to detect PPI-149 in the plasma beyond about day 8, the testosterone level results demonstrate that PPI-149 was still therapeutically active in vivo over the course of the experiment.

EXAMPLE 7

Figure 2:
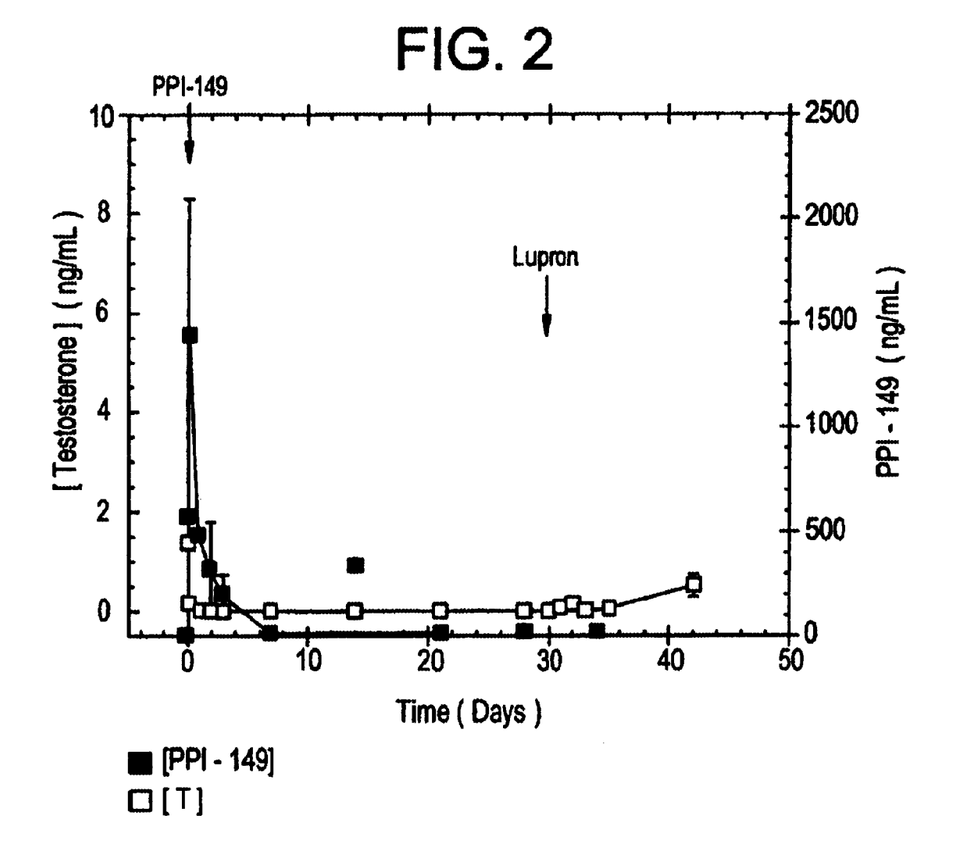
FIG. 2 is a graph depicting the plasma testosterone levels (in ng/ml; open boxes) and plasma PPI-149 levels (in ng/ml; closed boxes) in rats over time following intramuscular injection of a complex of the LHRH antagonist PPI-149 and carboxymethylcellulose on day 0 and injection of the LHRH agonist Lupron™ at day 30, demonstrating suppression of the Lupron™-induced testosterone surge by the PPI-149 pretreatment.

A water-insoluble complex of the LHRH antagonist PPI-149 and carboxymethylcellulose was prepared according to the preceding examples. A suspension of the PPI-149/CMC complex was prepared and a single dose was injected intramuscularly into rats on day 0. On day 30, the LHRH agonist Lupron™ (leuprolide) was injected into the rats. Plasma testosterone levels (in ng/ml; indicated by the open boxes in FIG. 2) were determined at various time points as a measure of the activity of the LHRH antagonist in the animal. Plasma levels of PPI-149 (in ng/ml) were also monitored in the animals (indicated by the closed boxes in FIG. 2). Representative results, shown in the graph of FIG. 2, demonstrate that pretreatment with the PPI-149/CMC complex rapidly reduces plasma testosterone to castration levels and, moreover, blocks the LHRH agonist-induced testosterone surge. Despite the inability to detect PPI-149 in the plasma beyond about day 8, the testosterone level results demonstrate that PPI-149 was still therapeutically active in vivo over the course of the experiment.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A pharmaceutical composition comprising a solid ionic complex of a pharmaceutically active peptide and a carrier macromolecule, wherein the peptide content of said complex is at least 57% by weight.

2. A pharmaceutical composition consisting essentially of a solid ionic complex of a pharmaceutically active peptide and a carrier macromolecule, wherein the peptide content of said complex is at least 57% by weight.

3. The pharmaceutical composition of any one of claim 1 or 2, wherein said pharmaceutically active peptide is an LHRH analogue.

4. The pharmaceutical composition of claim 3 wherein said pharmaceutically active peptide is an LHRH antagonist.

5. The pharmaceutical composition of any one of claim 1 or 2, wherein said pharmaceutically active peptide is selected from the group consisting of bradykinin analogues, parathyroid hormone, adenocorticotrophic hormone, calcitonin, and vasopressin analogues.

6. The pharmaceutical composition of any one of claim 1 or 2, wherein the pharmaceutically active peptide is cationic and the carrier macromolecule is anionic.

7. The pharmaceutical composition of any one of claim 1 or 2, wherein the complex provides sustained delivery of the pharmaceutically active peptide to a subject for at least one week after the pharmaceutical composition is administered to the subject.

8. The pharmaceutical composition of any one of claim 1 or 2, wherein the complex provides sustained delivery of the pharmaceutically active peptide to a subject for at least two weeks after the pharmaceutical composition is administered to the subject.

9. The pharmaceutical composition of any one of claim 1 or 2, wherein the complex provides sustained delivery of the pharmaceutically active peptide to a subject for at least three weeks after the pharmaceutical composition is administered to the subject.

10. The pharmaceutical composition of any one of claim 1 or 2, wherein the complex provides sustained delivery of the pharmaceutically active peptide to a subject for at least four weeks after the pharmaceutical composition is administered to the subject.

11. The pharmaceutical composition of any one of claim 1 or 2, wherein the pharmaceutically active peptide is a multivalent cationic or anionic peptide.

12. The pharmaceutical composition of any one of claim 1 or 2, wherein the peptide is 5 to 20 amino acids in length.

13. The pharmaceutical composition of any one of claim 1 or 2, wherein the peptide is 8 to 15 amino acids in length.

14. The pharmaceutical composition of any one of claim 1 or 2, wherein the peptide is 8 to 12 amino acids in length.

15. The pharmaceutical composition of any one of claim 1 or 2, wherein the carrier macromolecule is an anionic polymer.

16. The pharmaceutical composition of any one of claim 1 or 2, wherein the carrier macromolecule is an anionic polyalcohol.

17. The pharmaceutical composition of any one of claim 1 or 2, wherein the carrier macromolecule is an anionic polysaccharide.

18. The pharmaceutical composition of any one of claim 1 or 2, wherein the carrier macromolecule is carboxymethylcellulose.

19. The pharmaceutical composition of any one of claim 1 or 2, wherein the carrier macromolecule is selected from the group consisting of algin, alginate, anionic acetate polymers, anionic acrylic polymers, xantham gums, anionic carageenan, anionic polygalacturonic acid, sodium starch glycolate, and pharmaceutically acceptable salts thereof.

20. The pharmaceutical composition of any one of claim 1 or 2, which is a lyophilized solid.

21. The pharmaceutical composition of any one of claim 1 or 2, wherein said solid ionic complex is suspended as a liquid suspension or dispersed as a semi-solid dispersion.

22. The pharmaceutical composition of claim 3 wherein the LHRH analogue is an LHRH antagonist comprising a peptide compound, wherein a residue of the peptide compound corresponding to the amino acid at position 6 of natural mammalian LHRH comprises a D-asparagine structure.

23. The pharmaceutical composition of claim 3 wherein the LHRH analogue is an LHRH antagonist comprising a peptide compound comprising a structure:

A-B-C-D-E-F-G-H-I-J wherein

A is pyro-Glu, Ac-D-Nal, Ac-D-Qal, Ac-Sar, or Ac-D-Pal

B is His or 4-Cl-D-Phe

C is Trp, D-Pal, D-Nal, L-Nal, D-Pal(N-O), or D-Trp

D is Ser

E is N-Me-Ala, Tyr, N-Me-Tyr, Ser, Lys(iPr), 4-Cl-Phe, His, Asn, Met, Ala, Arg or Ile;

F is D-Asn, D-Gln, or D-Thr;

G is Leu or Trp;

H is Lys(iPr), Gln, Met, or Arg

I is Pro; and

J is Gly-NH$_2$ or D-Ala-NH$_2$;

or a pharmaceutically acceptable salt thereof.

24. A pharmaceutical composition comprising a solid ionic complex of an LHRH analogue and a carrier macromolecule, wherein the LHRH analogue content of said complex is at least 57% by weight.

25. A pharmaceutical composition consisting essentially of a solid ionic complex of an LHRH analogue and a carrier macromolecule, wherein the LHRH analogue content of said complex is at least 57% by weight.

26. The pharmaceutical composition of any one of claim 24 or 25, wherein the LHRH analogue is an LHRH antagonist having the following structure: Ac-D-Nal-4-Cl-D-Phe-D-Pal-Ser-N-Me-Tyr-D-Asn-Leu-Lys(iPr)-Pro-D-Ala.

27. The pharmaceutical composition of any one of claim 24 or 25, wherein the complex provides sustained delivery of the LHRH analogue to a subject for at least one week after the pharmaceutical composition is administered to the subject.

28. The pharmaceutical composition of any one of claim 24 or 25, wherein the complex provides sustained delivery of the LHRH analogue to a subject for at least two weeks after the pharmaceutical composition is administered to the subject.

29. The pharmaceutical composition of any one of claim 24 or 25, wherein the complex provides sustained delivery of the LHRH analogue to a subject for at least three weeks after the pharmaceutical composition is administered to the subject.

30. The pharmaceutical composition of any one of claim 24 or 25, wherein the complex provides sustained delivery of the LHRH analogue to a subject for at least four weeks after the pharmaceutical composition is administered to the subject.

31. The pharmaceutical composition of any one of claim 24 or 25, wherein the LHRH analogue is a multivalent cationic or anionic peptide.

32. The pharmaceutical composition of any one of claim 24 or 25, wherein the LHRH analogue is 5 to 20 amino acids in length.

33. The pharmaceutical composition of any one of claim 24 or 25, wherein the LHRH analogue is 8 to 15 amino acids in length.

34. The pharmaceutical composition of any one of claim 24 or 25, wherein the LHRH analogue is 8 to 12 amino acids in length.

35. The pharmaceutical composition of any one of claim 24 or 25, wherein the LHRH analogue is an LHRH antagonist comprising a peptide compound, wherein a residue of the peptide compound corresponding to the amino acid at position 6 of natural mammalian LHRH comprises a D-asparagine structure.

36. The pharmaceutical composition of any one of claim 24 or 25, wherein the LHRH analogue is an LHRH antagonist comprising a peptide compound comprising a structure:

A-B-C-D-E-F-G-H-I-J wherein

A is pyro-Glu, Ac-D-Nal, Ac-D-Qal, Ac-Sar, or Ac-D-Pal

B is His or 4-Cl-D-Phe

C is Trp, D-Pal, D-Nal, L-Nal, D-Pal(N-O), or D-Trp

D is Ser

E is N-Me-Ala, Tyr, N-Me-Tyr, Ser, Lys(iPr), 4-Cl-Phe, His, Asn, Met, Ala, Arg or Ile;

F is D-Asn, D-Gln, or D-Thr;

G is Leu or Trp;

H is Lys(iPr), Gln, Met, or Arg

I is Pro; and

J is Gly-NH$_2$ or D-Ala-NH$_2$;

or a pharmaceutically acceptable salt thereof.

* * * * *